US012642519B2

(12) United States Patent
Pelletier et al.

(10) Patent No.: US 12,642,519 B2
(45) Date of Patent: Jun. 2, 2026

(54) TISSUE ENGAGEMENT DEVICE AND METHOD

(71) Applicant: NewSouth Innovations Pty Limited, Sydney (AU)

(72) Inventors: Matthew Pelletier, Sydney (AU); William Walsh, Sydney (AU)

(73) Assignee: NewSouth Innovations Pty Limited, Sydney (AU)

( * ) Notice: Subject to any disclaimer, the term of this patent is extended or adjusted under 35 U.S.C. 154(b) by 334 days.

(21) Appl. No.: 18/037,855

(22) PCT Filed: Nov. 18, 2021

(86) PCT No.: PCT/AU2021/051375
§ 371 (c)(1),
(2) Date: May 19, 2023

(87) PCT Pub. No.: WO2022/104425
PCT Pub. Date: May 27, 2022

(65) Prior Publication Data
US 2024/0108324 A1 Apr. 4, 2024

(30) Foreign Application Priority Data
Nov. 20, 2020 (AU) ................................ 2020904290

(51) Int. Cl.
*A61B 17/04* (2006.01)

(52) U.S. Cl.
CPC .. *A61B 17/0401* (2013.01); *A61B 2017/0409* (2013.01); *A61B 2017/0412* (2013.01); *A61B 2017/0417* (2013.01); *A61B 2017/042* (2013.01); *A61B 2017/0464* (2013.01)

(58) Field of Classification Search
CPC ........ A61B 17/0401; A61B 2017/0495; A61B 17/0466; A61B 17/06166; A61B 2017/0406; A61B 2017/0464; A61F 2/0811; A61F 2/0063
See application file for complete search history.

(56) References Cited

U.S. PATENT DOCUMENTS

| | | | |
|---|---|---|---|
| 2006/0247641 A1 | 11/2006 | Re et al. | |
| 2012/0296375 A1 | 11/2012 | Thal | |
| 2014/0155938 A1 | 6/2014 | Anderson | |
| 2017/0215865 A1 | 8/2017 | Sengun et al. | |

FOREIGN PATENT DOCUMENTS

WO 2016049081 A1 3/2016

*Primary Examiner* — Katherine M Shi
(74) *Attorney, Agent, or Firm* — The Webb Law Firm

(57) ABSTRACT

Disclosed is a soft tissue engagement device. The soft tissue engagement device includes a substantially rigid elongate body extending from a first end to a second end. The elongate body is configured to be inserted at least partially within the soft tissue, transverse to a load-bearing direction of the tissue. The elongate body is further configured to engage sutures attached to underlying suture-anchors secured to a bone, thereby to draw the soft tissue onto the bone. Also disclosed is a method for attaching soft tissue to a bone.

6 Claims, 10 Drawing Sheets

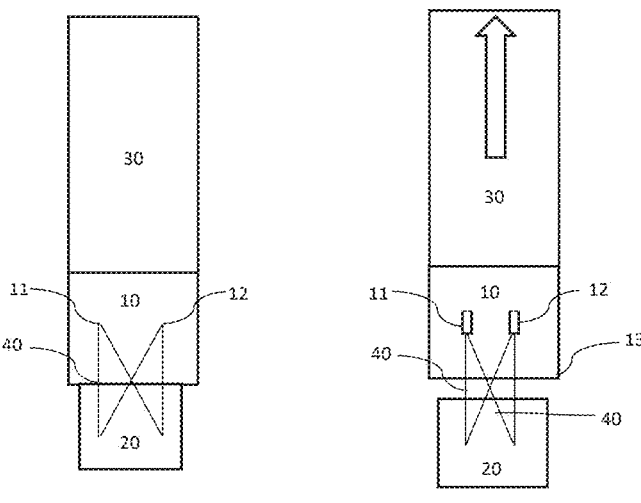
*Fig 1A*
PRIOR ART
*Fig 1B*
PRIOR ART
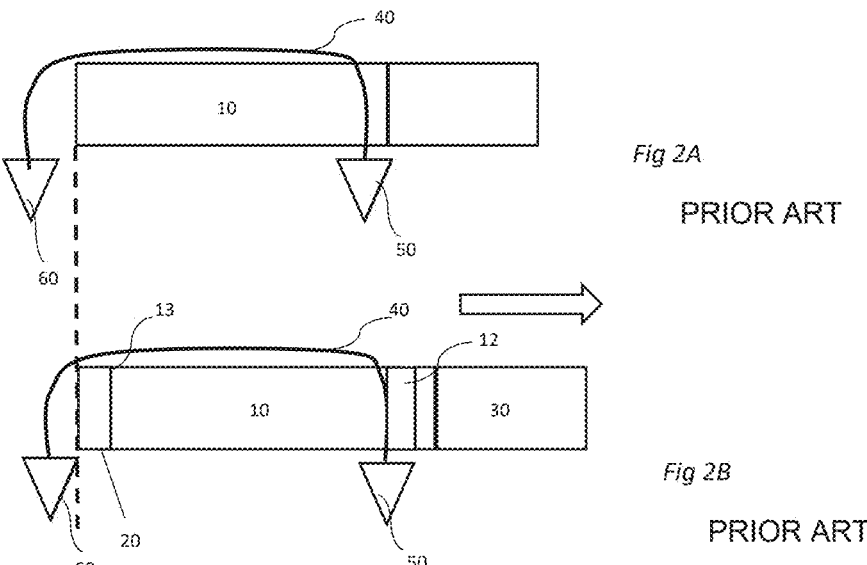
*Fig 2A*
PRIOR ART
*Fig 2B*
PRIOR ART

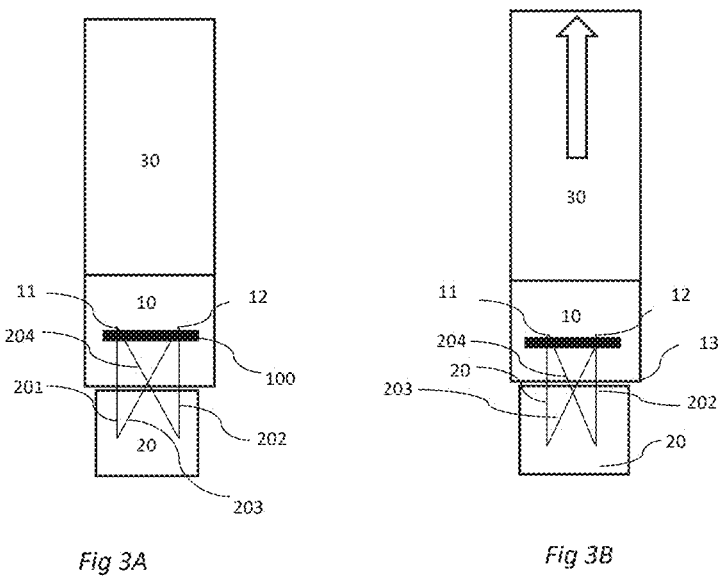
Fig 3A                    Fig 3B
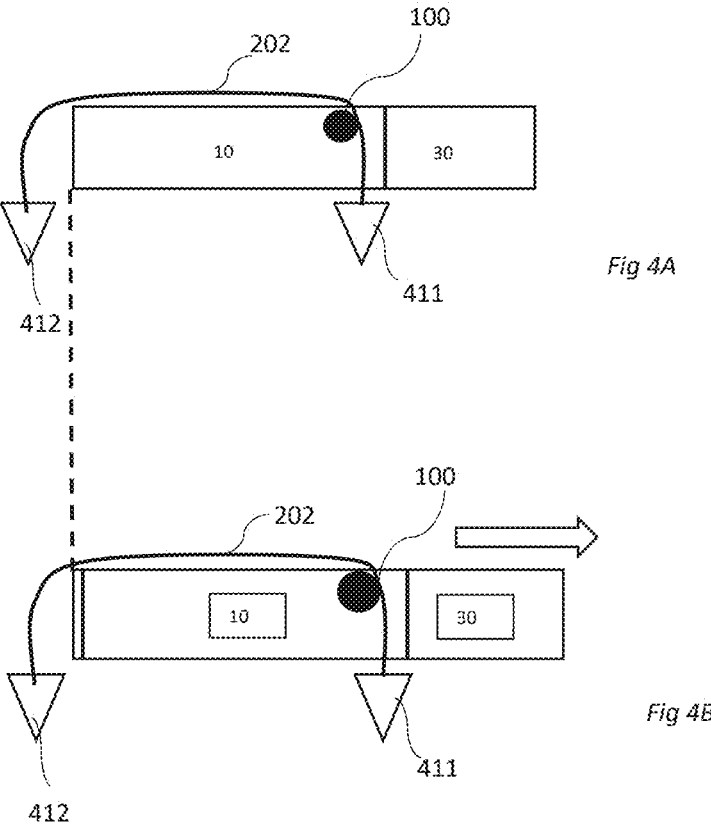
Fig 4A
Fig 4B

120

100i

121

122a

121

100j 132a        131a

100k

130

131b        132b

TISSUE ENGAGEMENT DEVICE AND METHOD

CROSS-REFERENCE TO RELATED APPLICATIONS

This application is the United States national phase of International Application No. PCT/AU2021/051375 filed Nov. 18, 2021, and claims priority to Australian Patent Application No. 2020904290 filed Nov. 20, 2020, the disclosures of which are hereby incorporated by reference in their entireties.

BACKGROUND OF THE INVENTION

Field of the Invention

The present disclosure relates to a device and method for engaging biological tissue.

Description of Related Art

Injury may result in complete or partial detachment of soft tissues such as ligaments or tendons from bone, or in complete or partial severing of the soft tissue.

The current standard of care for repairing such injuries is to re-attach the detached end of the tissue to the bone, or to re-attach the severed ends of the tissue. This is typically achieved using sutures, which are passed through the soft tissue. In the case of reattachment to bone, the sutures may be affixed to anchors inserted into the bone to which the tissue is to be approximated. The repair must have sufficient strength to prevent excursion of the tissue away from the intended attachment site during loading of the tissue. Accordingly, many varying suturing techniques and patterns have been developed with the aim of providing adequate tensile strength to the repair site.

However, when the repair is placed under load, the force is concentrated over the relatively small surface area provided by the sutures. As a result, the sutures may cut longitudinal slits through the tissue before ultimate failure of the repair. This phenomenon is sometimes referred to a "cheese wiring", as the mechanism is similar to that of a wire cheese cutter slicing through a block of cheese. This can lead to damage of the local tissue as well as a loss of the original fixation position established by the repair.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each of the appended claims.

SUMMARY OF THE INVENTION

According to one aspect of the present disclosure, there is provided a soft tissue engagement device comprising a substantially rigid elongate body extending from a first end to a second end, the elongate body configured to be inserted at least partially within the soft tissue, transverse to a load-bearing direction of the tissue and configured to engage sutures attached to underlying suture-anchors secured to a bone, thereby to draw the soft tissue onto the bone.

According to another aspect of the present disclosure, there is provided a soft tissue engagement device comprising a substantially rigid elongate body extending from a first end to a second end, the elongate body configured to be inserted at least partially within the soft tissue, transverse to a load-bearing direction of the tissue and configured to engage underlying anchors secured to a bone, thereby to draw the soft tissue onto the bone.

The device typically sits transverse to the load-bearing direction of the tissue in its final position. It may however be inserted at various angles before being moved into its final position. For example, the device may be inserted initially in a parallel, perpendicular or oblique to the load bearing direction.

Further, in its final position, the device typically sits parallel to the greatest width of the tissue. That is, in a tendon, the device is typically implanted parallel to the width of the tendon, rather than the parallel to the thickness of the tendon. For example, when used for repair of an Achilles tendon, the device would typically extend in the lateromedial direction, rather than the anteroposterior direction.

The soft tissue may be any soft tissue requiring repair including but not limited to a tendon, ligament, muscle, cartilage or in some embodiments it is envisaged that the device may be used with tissue such as bone. The device may be used to repair a soft tissue tear, separation or other damage. In one embodiment, the soft tissue is a tendon and the damage to be repaired is a tear or complete rupture of the tendon or a separation of the tendon from a bone. In other embodiments the soft tissue includes connective tissue such as but not limited to skin, vascular tissue and nerve tissue.

The elongate body of the soft tissue engagement device may be resiliently flexible to provide sufficient rigidity structurally but also to allow some degree of flexibility to aid the insertion and positioning in the soft tissue should this be necessary. The device may also provide a dynamic load for the soft tissue to facilitate healing by, for example, recovering any elastic deformation applied as a result of loading or by changing direction of loading due to the position in the tissue.

The elongate body may be configured such that it is deformable to substantially conform to the underlying bone when implanted. Conforming to the underlying bone may improve footprint area and distribution of load onto the bone The elongate body may be configured to be permanently deformable. For example, the elongate body may have a relatively high modulus of elasticity, such that it holds its shape under load, but may be permanently deformable (or pre-formed) for contouring to the underlying bone. In other embodiments, the elongate body may have a relative low modulus of elasticity, such that it deforms under load. In such embodiments, the elongate body may be resiliently deformable, such that it returns to its original shape when the load is removed.

In some embodiments, the elongate body may be substantially straight. The straight elongate body may be configured to conform to the surface of the underlying bone substantially as described above. In other embodiments, the elongate body may be curved. For example, the elongate member may be contoured such that, when implanted, it substantially conforms to the surface of the underlying bone without deformation or with minimal deformation. In other embodiments, the curvature of the elongate member may be less than that of the bone, such that deformation of the elongate body is required to increase the curvature of the elongate body for conformation to the bone surface. In still further embodiments, the elongate body may be over-contoured. That is, the elongate body may have a curvature greater than that of the bone such that deformation of the elongate body is required to decrease the curvature of the elongate body for conformation to the bone surface. Such embodiments may provide increased force between the elongate body and the bone at or adjacent the ends of the elongate body.

The elongate body may have a substantially uniform cross section along its entire length. In other embodiments, the elongate body may comprise portions having relatively greater cross-sectional area. For example, the elongate body may taper along its length from the first end to the second end (or from the second end to the first end). Alternatively, the elongate body may comprise a middle portion having a relatively greater cross-sectional area and taper towards both the first and second ends. In other embodiments, the first and second ends may have a relatively greater cross-sectional area. For example, one or both of the first and second ends may comprise retention lugs configured to inhibit the respective end of the elongate body from entering the soft tissue.

The elongate body may be circular in cross section. Alternatively, the elongate body may comprise a flattened plate, an ovoid, square, rectangular, triangular, elliptical or crescent shaped cross section. The cross section may also include periodic spikes, hooks or other features to retain position in the soft tissue.

In some embodiments, the elongate body is configured to engage sutures adjacent to the first and second ends. An exterior surface of the elongate body may be at least partially roughened, etched, porous or ribbed to grip the sutures. In some embodiments, the elongate body may include grooves, slots or ridges defining suture engaging regions. The sutures may be connected to the inside of the device or on an external surface.

In other embodiments, the device may engage the anchors directly, negating the need for sutures. The device may comprise one or more anchor engaging portions. For example, the elongate body may include one or more apertures, eyelets, hooks or other anchor engaging elements.

The elongate body may be made from a metal or a metal alloy or alternatively may be made from a polymeric material. Examples of suitable materials include stainless steel and its alloys, titanium and its alloys, cobalt chrome and its alloys, tantalum and its alloys, polyether ether ketone (PEEK), MP35N and its alloys, graphite/pyrocarbon.

In some embodiments, the elongate body is at least partially made from a bio-resorbable material. The elongate body may be made from collagen, chitosan or synthetic polymers including poly (glycolic acid) (PGA), poly (lactic acid) (PLA) and poly (lactic-co-glycolide) (PLGA), a bio-ceramic material including tricalcium phosphate (TCP) or hydroxyapatatite (HA). The bio-resorbable materials may also contain chemotactic agents or therapeutics that encourage a biological response, such as vascular ingrowth.

The elongate body may be made from a radiolucent or radiopaque material.

Also disclosed is a method of attaching a soft tissue to a bone, the method comprising:

inserting a soft tissue engagement device into the soft tissue and transverse to a load bearing direction of the soft tissue, wherein the soft tissue engagement device comprises a substantially rigid elongate body extending from a first end to a second end, the elongate body configured to engage sutures attached to one or more suture-anchors secured to a bone;

passing sutures from the suture-anchors through the soft tissue medially to the soft tissue engagement device;

passing the sutures over the soft tissue engagement device; and subsequently, securing each of the sutures to a suture-anchor.

In this embodiment, the soft tissue may be a tendon. While an example is provided of a tendon, it is to be understood that the method may be equally utilised for attaching another soft tissue to the bone such as for example a ligament.

A tendon for repair may extend from a musculotendinous junction to an end which is typically secured to bone. In some cases, the tendon is damaged and comes away from the bone to result in an unsecured tendon end. It is necessary in such a repair to secure the unsecured end again to the bone. The term "medial" or "medially" as used herein relates to a position towards the join of the tendon with the muscle whereas "lateral" or "laterally" refers to a position towards or beyond the unsecured end of the tendon in its damaged state. An example of repair is a repair of a rotator cuff tendon. In repairs other than a rotator cuff, it should be understood that the term "medial" may be replaced with the term "proximal" and the term "lateral" with the term "distal".

The soft tissue engagement device may be a tendon engagement device. The one or more suture anchors may comprise two medial anchors which are typically positioned substantially inferior and in-line with the tendon engagement device in the underlying bone. The suture anchors typically comprise one or more sutures attached at one end to the anchor and extending to a free end.

Once the medial anchor(s) are secured to the bone, the tendon may be manipulated by a surgeon to bring the unsecured end into the correct positioning over the region of bone which provides a footing for the tendon including by increasing the contact area between the tendon and bone tissue to facilitate healing.

Once the tendon is correctly positioned, a suture attached to a first medial anchor is passed through the tendon tissue, medial to the tendon engagement device, over the tendon engagement device and secured back to the same medial anchor. The same process may be performed with a second or more medial anchors and associated sutures.

The above method provides "medial securement" of the tendon to the underlying bone. Such medial securement provides a relatively rigid attachment of the tendon to the bone due to the fact that the suture length is relatively short resulting in minimal elongation of the sutures and little slack as load is applied to the tendon by muscle contraction. A surgeon may, however also wish to secure the tendon to the bone at a lateral location.

The steps outlined below may be in addition to the medial securement steps described above or may replace them. One or more medial anchor(s) may be secured to the bone in-line and inferior to the tendon engagement device. One or more lateral anchors may also be secured to the bone at a location lateral to the desired position of the unsecured end of the tendon. Each anchor may have one or more associated suture. In this embodiment, the medial anchors have a suture affixed at a first end to the anchor and extending to a free end. Once the tendon is correctly positioned, a suture attached to a first medial anchor is passed through the tendon tissue, medial to the tissue engagement device, over the tendon engagement device and drawn in a lateral direction either across an outer surface of the tendon, or alternatively through the tendon tissue before being secured to a first lateral anchor. The suture typically applies a downward force on the tendon, forcing the tendon towards the underlying bone. The same process may be performed with a second or more medial anchors wherein the sutures of each medial anchor may be secured to one or more lateral anchors.

In one embodiment, the method further provides:

fastening a first medial anchor to the bone;

fastening a second medial anchor to the bone, spaced from the first medial anchor;

fastening a first lateral anchor to the bone at a location lateral to the first and second medial anchors;

fastening a second lateral anchor to the bone, spaced from the first lateral anchor;

providing a first suture having a fixed end a free end, the fixed end secured to the first medial anchor and passing the free end through the tendon tissue medial to the tissue engagement device and securing the free end to the first lateral anchor; and providing a second suture having a fixed end a free end, the fixed end secured to the second medial anchor and passing the free end through the tendon tissue medial to the tissue engagement device and securing the free end to the second lateral anchor.

The method may further provide:

providing a third suture having a fixed end a free end, the fixed end secured to the first medial anchor and passing the free end through the tendon tissue medial to the tissue engagement device and securing the free end to the second lateral anchor;

providing a fourth suture having a fixed end a free end, the fixed end secured to the second medial anchor and passing the free end through the tendon tissue medial to the tissue engagement device and securing the free end to the first lateral anchor.

In another aspect, disclosed is a method of attaching a soft tissue to bone, the method comprising:

inserting a soft tissue engagement device into the soft tissue and transverse to a load bearing direction of the soft tissue, wherein the soft tissue engagement device comprises a substantially rigid elongate body extending from a first end to a second end, the elongate body configured to engage one or more anchors secured to a bone;

securing the one or more anchors to the device.

In this embodiment, it will be appreciated that sutures are not required as the soft tissue engagement device is configured to directly engage the anchors.

In some embodiments, the one or more anchors may be inserted through the soft tissue and secured to the bone subsequently to inserting the soft tissue engagement device. The one or more anchors may be inserted through the soft tissue engagement device and subsequently secured to the bone. The one or more anchors may be inserted substantially perpendicularly to the elongate body. The one or more anchors may pass through a respective one or more apertures or engagement features of the soft tissue engagement device. The connection of the anchors to the soft tissue engagement device may be by means of a rivet or hook and eye connection. In other embodiments, the connection may be threaded.

The soft tissue engagement device and/or the anchors may be inserted using a guide or jig. The guide may aid in insertion and alignment of the soft tissue engagement device and/or anchors. For example, the guide may comprise a sliding arm configured to insert the soft tissue device through the soft tissue transverse to a load bearing direction of the soft tissue. The guide may further comprise one or more punch members configured to insert the anchors through the soft tissue and into the bone.

In another aspect, a method for repair of a soft tissue which is separated into separate portions is described, the method including:

inserting a first soft tissue engagement device into a first portion of the soft tissue and transverse to a load bearing direction of the soft tissue, wherein the soft tissue engagement device comprises a substantially rigid elongate body extending from a first end to a second end;

inserting a second soft tissue engagement device into a second portion of the soft tissue and transverse to a load bearing direction of the soft tissue, wherein the soft tissue engagement device comprises a substantially rigid elongate body extending from a first end to a second end;

securing the two soft tissue engagement devices to each other by one or more sutures.

The device of the present disclosure may be used in repair of a severed or at least partially severed tendon. An example is the repair of an Achilles tendon. In this embodiment the device of the disclosure may be inserted into one tendon end and a second device inserted into the other tendon end. Sutures may be applied across the gap between the tendon ends to attach to each device to thereby bring the ends of the tendon together. The positioning of the two devices prevents "cheese wiring" of the tendon ends by the sutures and loss of repair position.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

BRIEF DESCRIPTION OF THE DRAWINGS

By way of example only, embodiments are now described with reference to the accompanying drawings, in which:

FIGS. 1A and 1B show a top view of a tendon repair method of the prior art in an unloaded and loaded configuration, respectively;

FIGS. 2A and 2B show a side view of the tendon repair method of FIGS. 1A and 1B in an unloaded and loaded configuration, respectively;

FIGS. 3A and 3B show a top view of a tendon repair method using a soft tissue engagement device according to an embodiment of the present disclosure in an unloaded and loaded configuration, respectively;

FIGS. 4A and 4B show a side view of the tendon repair of FIGS. 3A and 3B in an unloaded and loaded configuration, respectively;

DESCRIPTION OF THE INVENTION

Figure 5:
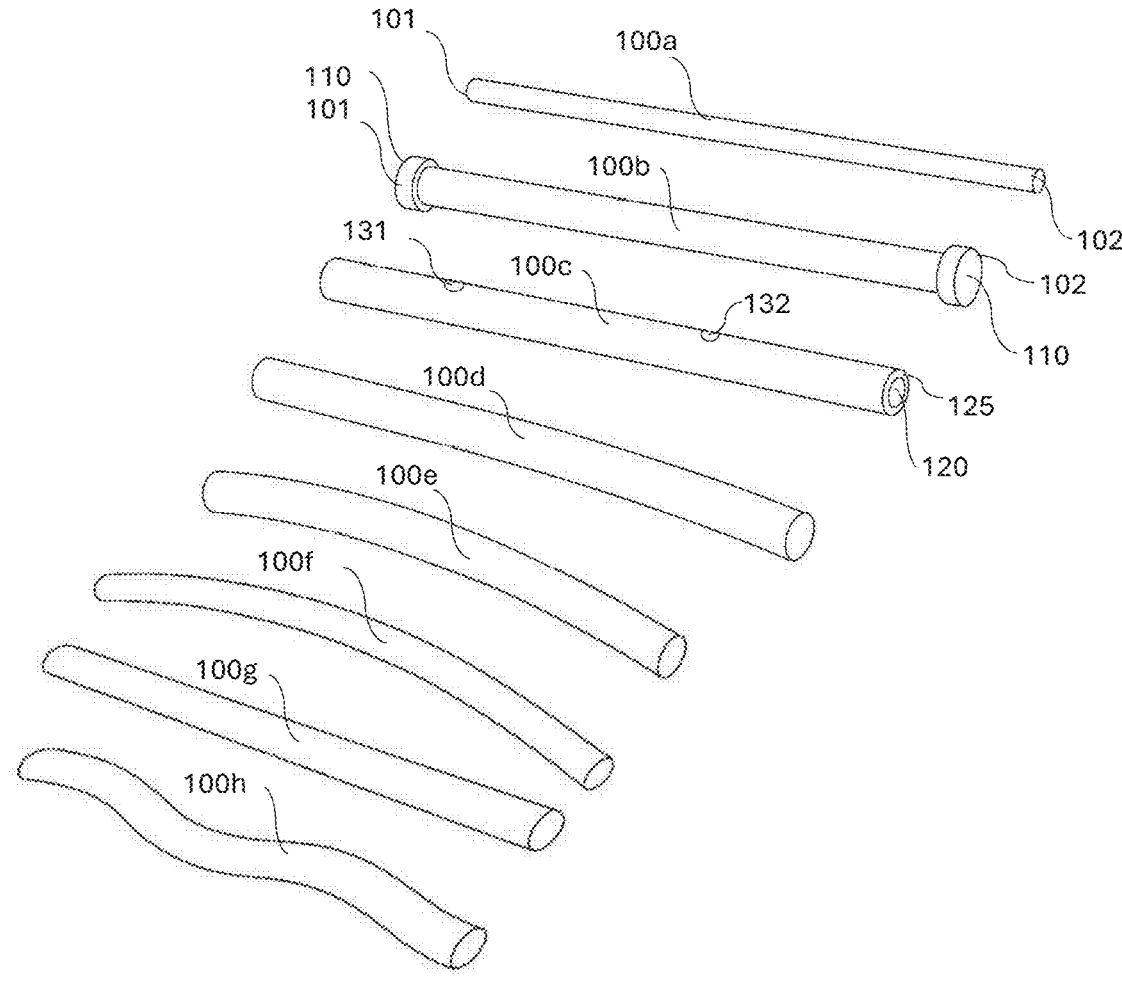
FIG. 5 shows soft tissue engagement devices according to several embodiments of the present disclosure.

A soft tissue engagement device of the present disclosure is generally shown as 100 in the drawings. The device may be used for tissue repair. For example, the device 100 may be used in reattaching of soft tissue to bone, or reattachments of severed ends of soft tissue to each other.

The examples refer primarily to repair of the rotator cuff tendon in which the tendon is reattached to bone. However, it should be understood that the device may be applicable in repair of any soft tissue, ligament or tendon or in tissue such as bone and in particular bones which are not weight bearing. As further examples, the device may be used in tendon to tendon repair, or tendon to bone repair, of rotator cuff tendon, Achilles tendon or patellar tendon. Further, the device may be used in reattachment of the ligament to bone, or ligament to ligament. For example, the device may be used in repair of the anterior cruciate ligament or posterior cruciate ligament. The invention is not limited to these specific applications and may be used in other procedures. Use of the disclosed device and method may improve resistance to suture cut-out or "cheese wiring" of the sutures through the tissue, thereby improving the tensile strength of the repair. Excessive micro-motion at the repair interface increases the challenge for the body to heal, resulting in increased loose connective tissue, and scar tissue formation that do not aid in function. The present device adds to the rigidity of the repair, reducing micro-motion at the interface, improving healing and function.

FIGS. 1A,1B, 2A and 2B show a tendon repair method of the prior art. The tendon 10 is secured to the bone 20 by sutures 40 which connect from a medial row of suture anchors 50 to a lateral row of suture anchors 60 in a suture bridge technique. However, upon application of force to the tendon 10 by muscle 30, the sutures 40 cut through the tendon 10 in a "cheese wiring" manner. The displacement of the sutures through the tendon 10 at points 11 and 12 is shown in FIGS. 1B and 2B. This displacement not only further damages the tendon 10 tissue, but also corresponds to a displacement of the lateral end 13 of the tendon 10 from its initial placement on the bone 20. This displacement of the lateral end 13 of the tendon 10 as a result of "cheese wiring" is non-recoverable and results in a loss of footprint between the tendon 10 and the bone 20. That is, the displacement results in a reduction in the available contact area between the tendon 10 and the bone 20 on which osseous integration is possible, reducing the efficacy of the repair. This failure injures the tendon and renders it with little mechanical integrity for salvage surgeries. The current invention also allows improved salvage properties following failure of a traditional suture bridge repair FIGS. 3A, 3B, 4A and 4B show a similar tendon repair, using tissue engagement device 100 according to the present disclosure. The tissue engagement device 100 is inserted at least partially intratendinously, transverse to the load-bearing direction of the tendon 10. Sutures 201, 202, 203, 204 are secured to the bone 20 and passed through the tendon 10 at points 11 and 12, medial to the tissue engagement device 100. The sutures 201, 202, 203, 204 are then secured to the bone 20. FIG. 4A shows the path of suture 202 from a medial anchor 411 to a lateral anchor 421. FIGS. 3B and 4B show the response of the tendon repair construct under load. Unlike the construct of FIGS. 1B and 2B, the force acting on the tendon 10 from the muscle 30 is not concentrated at points 11 and 12. Rather, the tissue engagement device 100 engages the sutures at points 11 and 12 and distributes the force applied by the sutures 201, 202, 203, 204 on the tissue of the tendon 10 across a greater surface area. This distribution of force increases the resistance of the repair construct to suture cut-out or "cheese wiring". Further, the use of a tissue engagement device according to the disclosure may decrease the time taken to perform a tissue repair operation by reducing the need for complex suture stitching techniques.

As shown in FIG. 4B, there may be some displacement of the lateral end 13 of the tendon 10 under load from its initial placement on the bone. However, in this instance, the displacement is primarily due to elastic deformation of the sutures 201, 202, 203, 204, rather than due to damage of the tissue of tendon 10 as shown in FIG. 2B. As such, the displacement is recoverable when the load is removed, and the contact footprint between the tendon 10 and the bone 20 is maintained.

FIG. 5 shows tissue engagement devices 100a-h according to several embodiments of the present disclosure. Each of the tissue engagement devices 100a-h is in the form of an elongate body extending from a first end 101 to a second end 102. The elongate body may be substantially straight, as in embodiments 100a-d and 100g, or may be curved or wavy as in embodiments 100e, 100f, and 100h.

In some embodiments, for example, as in devices 100a, 100b, 100c, 100d, 100e, the elongate body has a substantially circular cross-section. In other embodiments, for example as in devices 100f, 100g, 100h, the elongate body has an elliptical cross section. In other embodiments, other cross sectional shapes may be used.

In some embodiments, the elongate body may have a substantially constant cross section along its length (as in devices 100a, 100d, 100e, 100f, 100g and 100h). In other embodiments, the elongate body may have a cross section which varies along its length. One such example is shown in FIG. 100b, which includes a lug 110 at each of its first and second ends 101, 102. The lugs may be configured to substantially prevent slipping of the ends 101, 102 of the device 100b into the tissue. By contrast, embodiments without such lugs 110 may be configured to be wholly implantable in the tissue.

In some embodiments, for example as in device 100c, the device may comprise a side wall 120, defining an internal lumen 125. The lumen may be configured to received one or more sutures, wires, or a delivery device. Alternatively or additionally, the device may comprise one or more apertures which may extend wholly or partially through the device 100. For example, apertures 131, 132 of device 100c extend through the side wall 120 to the lumen 125. The suture may also be integral with the device or moulded into the device such that the suture is rigidly fixed and prevented from sliding therethrough.

Figures 6A, 6B, 6C:
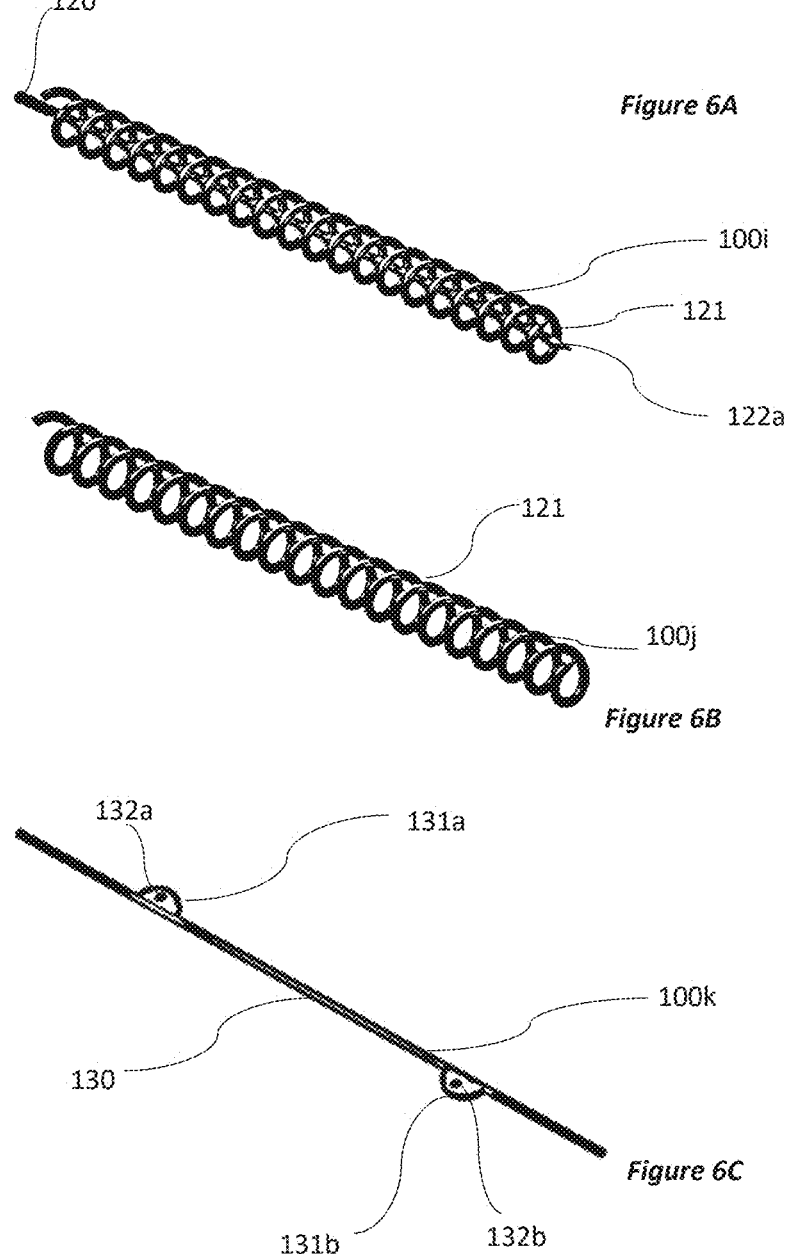
FIGS. 6A to 6F show soft tissue engagement devices according to several further embodiments of the present disclosure.

Further embodiments of the device are provided in FIGS. 6A to 6F. In FIG. 6A, the device 100i comprises a central shaft 120 centrally extending through helical member 121. End 122a is pointed to aid in the insertion through tissue.

Device 100*j* comprises helical member 121 without the central shaft 120.

Device 100*k* comprises an elongate body 130 having opposed lugs 131*a* and 131*b*. Each lug has an aperture 132*a* and 132*b* which may be used to receive a suture.

Figure 6D:
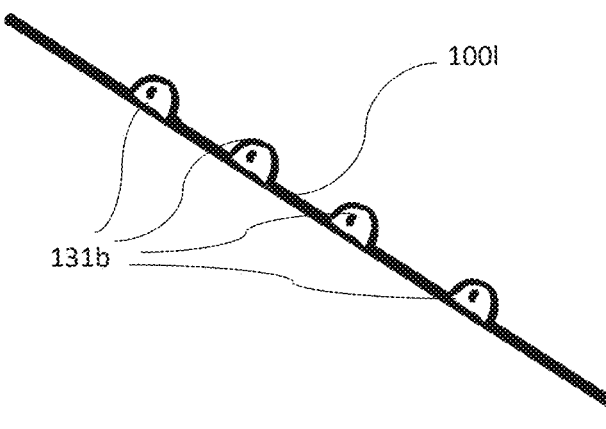
Figure 6E:
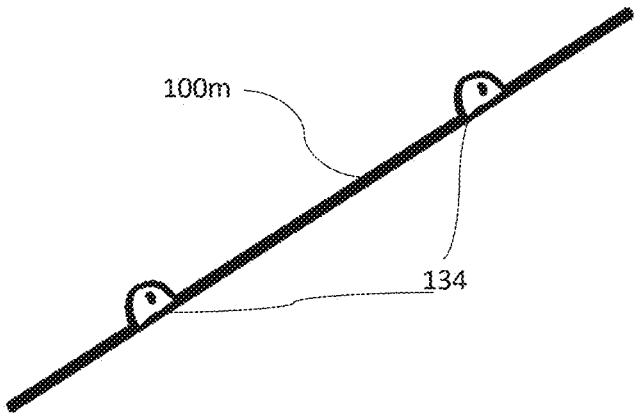
Figure 6F:
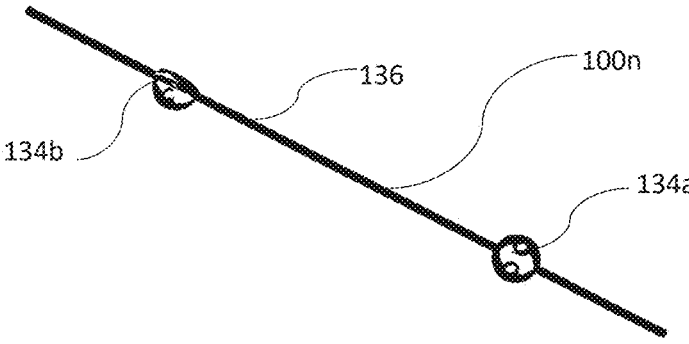

In FIG. 6D, the device 100*l* has four spaced lugs 133 which are aligned. Device 100*m* of FIG. 6E has two lugs 134.

Lugs 134*a* and 134*b* of device 100*n* provide another embodiment. Lug 134*a* extends on either side of shaft 136 and has two apertures positioned on opposite sides of the shaft 136. Lug 134*b* is angled in shape and has one half extending in a plane orthogonal to the other half.

The elongate body of the soft tissue engagement device may be configured such that it is deformable to substantially conform to the underlying bone when implanted. Examples such embodiments are shown in FIGS. 13A and 13B.

Figure 13A:
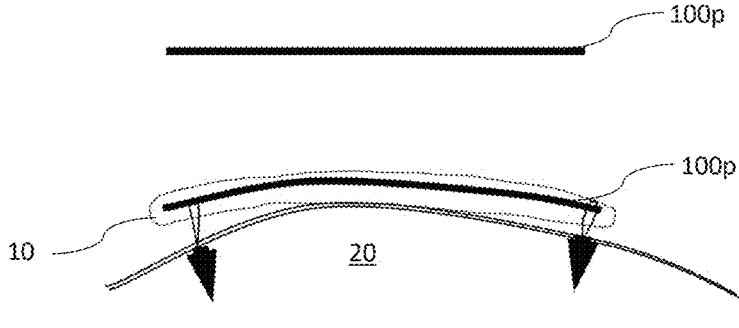
FIGS. 13A-13B show exemplary embodiments of the device of the present invention configured to be deformable to confirm when implanted.

The device 100*p* of FIG. 13A has a substantially straight elongate body. In this embodiment, the elongate body has a relatively high modulus of elasticity and is configured to deform to partially conform to the surface of the underlying bone 20, as shown in the lower portion of FIG. 13A. This results in a relatively low contact footprint area between the tendon 10 and the bone 20.

Figure 13B:
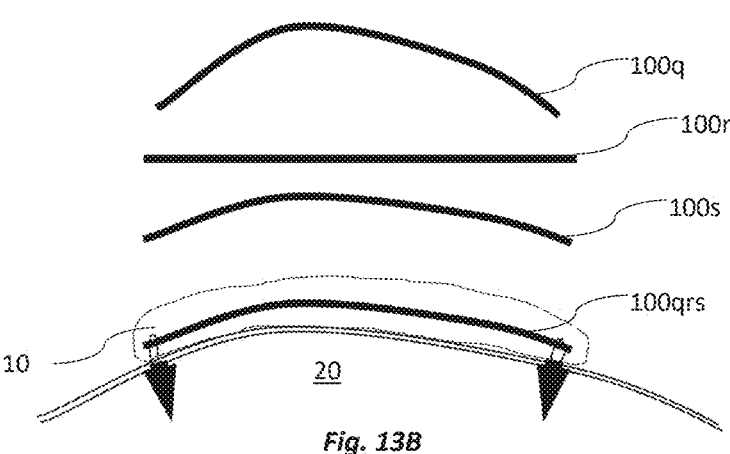

In other embodiments, for example devices 100*q*, 100*r* and 100*s* as shown in FIG. 13B, the elongate body has a lower modulus of elasticity and is configured to deform to conform to the curvature of the underlying bone under load. The initial configurations of the devices are shown at the top of FIG. 13B. Each of these devices conforms to the shape of the bone to take the final, implanted configuration as shown in the lower portion of FIG. 13B.

Device 100*r* is initially straight, as with device 100*p*. However, as device 100*r* is more flexible than device 100*p*, the final contact footprint area between the tendon and the bone in FIG. 13B is greater than in FIG. 13A.

Device 100*s* is curved to closely match the curvature of the bone such that minimal deformation is required to match the shape of the bone. Device 100*q* is over-contoured, that is, it has a curvature greater than that of the bone such that deformation is required to decrease the curvature of device 100*q* for conformation to the bone.

In one example, the tissue engagement device 100 may be used for repair of a detached rotator cuff tendon. The repair method may include steps as illustrated in FIGS. 7A to 7F. The surgery may be performed arthroscopically.

Figures 7A, 7B, 7C, 7D, 7E, 7F:
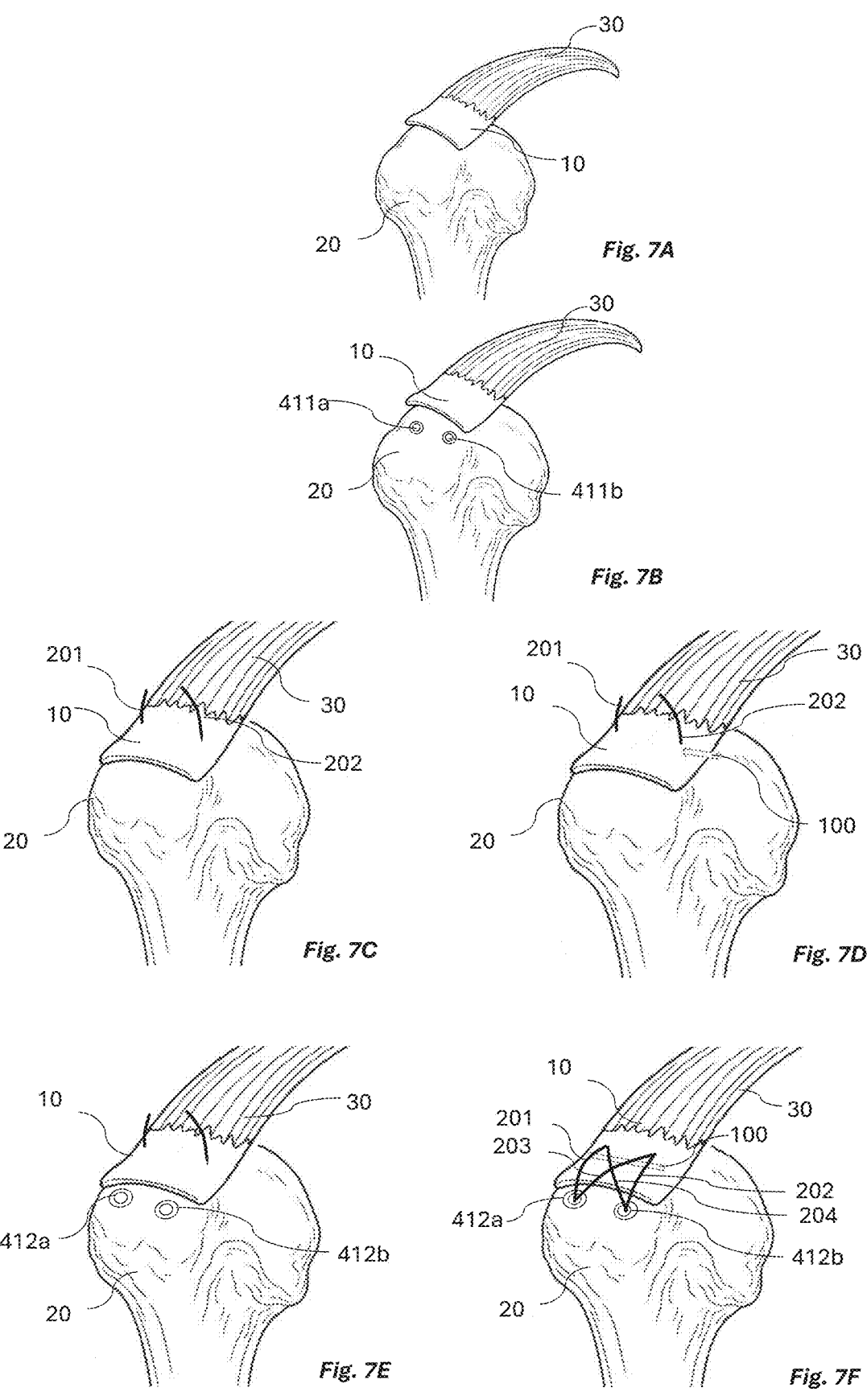
FIGS. 7A-7F illustrate steps in a method of attaching a tendon to a bone according to one embodiment of the present disclosure.

FIG. 7A shows the bone 20 and tendon 10 before the repair is commenced. In FIG. 7B, two medial anchors 411*a*, 411*b* are placed in the greater tuberosity of the bone 20. The tendon 10 is positioned over the bone 20 in a desired fixation location and sutures 201, 202, 203, 204 are passed from the medial anchors 411*a*, 411*b* through the tendon tissue, medial to the tissue engagement device 100, as shown in FIG. 7C.

The tissue engagement device 100 is then inserted intra-tendinously, lateral to the musculotendinous junction, such that an axis of the device 100 lies substantially orthogonal to an axis or loading direction of the rotator cuff tendon. In some embodiments, the tissue engagement device 100 may be inserted through a transverse incision in the tendon 10, or, in other embodiments, may be pushed through the tissue of the tendon without first making an incision. In other embodiments it is envisaged that the device may sit above the tendon on the bursal side or below the tendon on the articular side.

The sutures are then passed over the tissue engagement device 100 and secured to one or more anchors. FIG. 7E shows two lateral anchors 412*a*, 412*b* inserted in the bone

20, while FIG. 7F shows the sutures 201, 202, 203, 204 secured to the lateral anchors 412*a*, 412*b* to form a suture bridge. For illustrative purposes, the tendon 10 is shown as partially transparent in FIG. 7F, revealing the position of the tissue engagement device 100. However, in this embodiment, the device 100 is located wholly intratendinously.

In other embodiments, the tissue engagement device 100 may be woven through longitudinal fibres of the tendon 10. In some embodiments, the device 100 may be inserted to the tendon tissue such that it weaves in and out of the tendon tissue. As such, one or more portions of the device 100 may be extratendinous on the bursal side and/or the articular side of the tendon 10. In such embodiments, the extratendinous portions of the tissue engagement device 100 on the articular and/or the bursal side of the tendon 10 may be used as attachment points for sutures.

Figure 8:
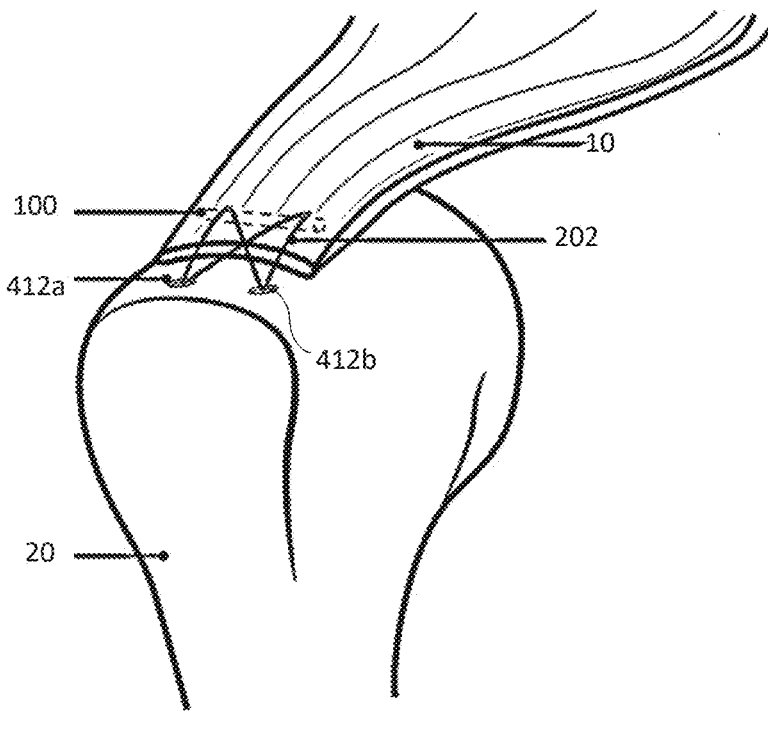
FIG. 8 shows a perspective view of a completed tendon repair using the method of FIGS. 7A-7F.
Figure 9:
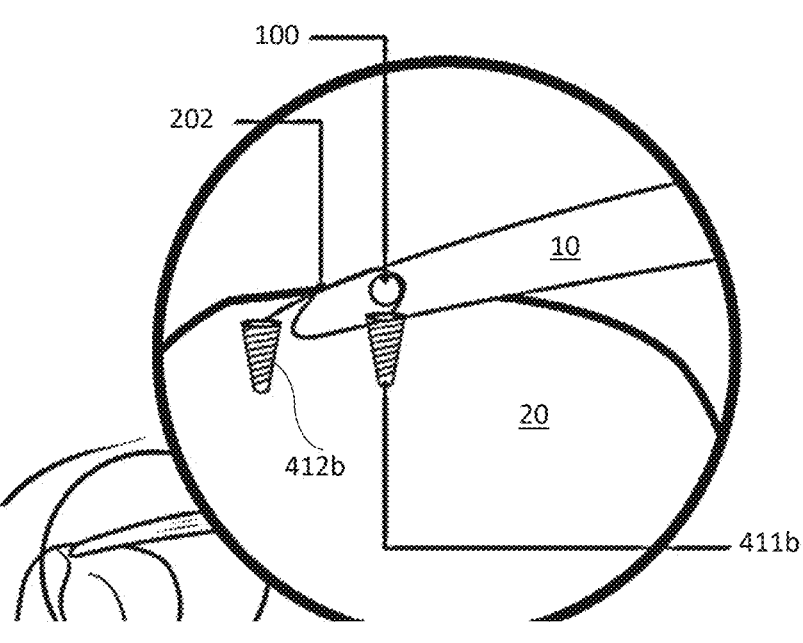
FIG. 9 shows an enlarged cross-section of the repair of FIG. 7.

FIGS. 8 and 9 show the completed repair according to the method of FIGS. 7A-H. The sutures 201, 202, 203, 204 passed from the medial anchors 411*a*, 411*b*, through the tissue of tendon 10 medial to the tissue engagement device 100, and are secured lateral anchors 412*a*, 412*b*. The tissue engagement device 100 engages the sutures 201, 202, 203, 204 adjacent each of its ends.

In other embodiments, the sutures 201, 202, 203, 204 may be secured to a single lateral anchor 415. In other embodiments, more than two lateral anchors may be used.

Figure 10:
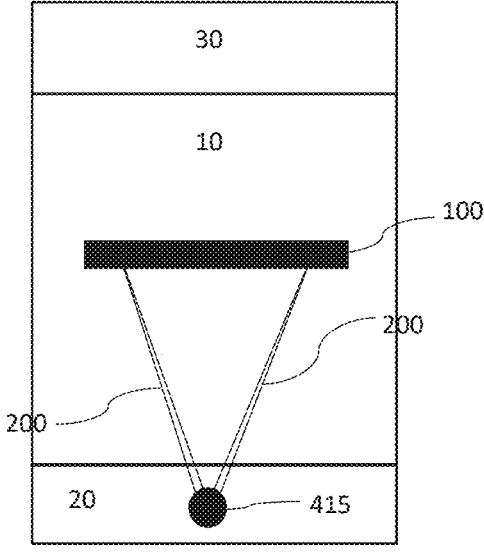
FIG. 10 shows a top view of a tendon repair according to another embodiment of the present disclosure.

In some embodiments, the medial anchors may be omitted. For example, as shown in FIG. 10, sutures 200 pass from lateral anchor 415 around the tissue engagement device 100 and are secured to the lateral anchor 415 (other embodiments may use more than one anchor). In other embodiments, the sutures may pass through a lumen or one or more apertures of the device 100 (for example, as shown in device 100*c* of FIG. 5). The omission of one or more anchors may reduce the overall cost of the repair procedure.

Figure 11:
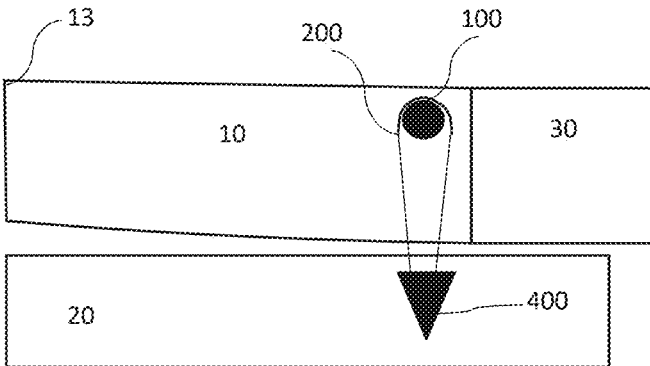
FIG. 11 shows a side view of a tendon repair method according to another embodiment of the present disclosure.

Alternatively, in some embodiments, lateral anchors may be omitted. For example, as shown in FIG. 11, suture 200 is passed from a medial anchor 400 through the tissue of tendon 10 and then secured to the medial anchor 400 such that the suture 200 encircles the tissue engagement device 100. In such embodiments, the suture length is significantly shortened compared to embodiments where the sutures are secured to a lateral row of anchors. This minimises potential migration of the tendon away from the attachment site due to elastic deformation of the sutures. In embodiments having one or more extratendinous portions of the tissue engagement device 100, sutures may be looped through extratendinous portions on the articular side of the tendon 10 and secured to medial anchors. This provides for improved rigidity of the connection between the tendon 10 and the bone 20 due to the shortened suture length.

However, where only a medial row of anchors is used, the lateral end 13 of the tendon 10 is left free and is not compressed onto the bone, as shown in FIG. 10. This may inhibit optimal healing. Accordingly, in some embodiments, an optional second set of sutures may pass from the medial anchors around the tissue engagement device and to a lateral anchor (or row of anchors) thereby to compress the lateral end of the tendon onto the bone. The demands of the second set of sutures in this configuration will be low as the majority of the load will be directed between the tendon, device and medial sutures/anchor(s).

Figure 14A:
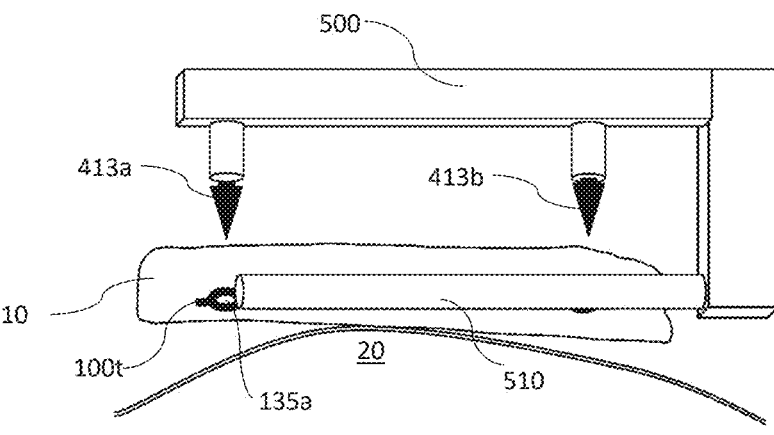
FIGS. 14A-14C show exemplary embodiments of a guide which assists in alignment and placement for use in conjunction with the present invention.
Figure 14B:
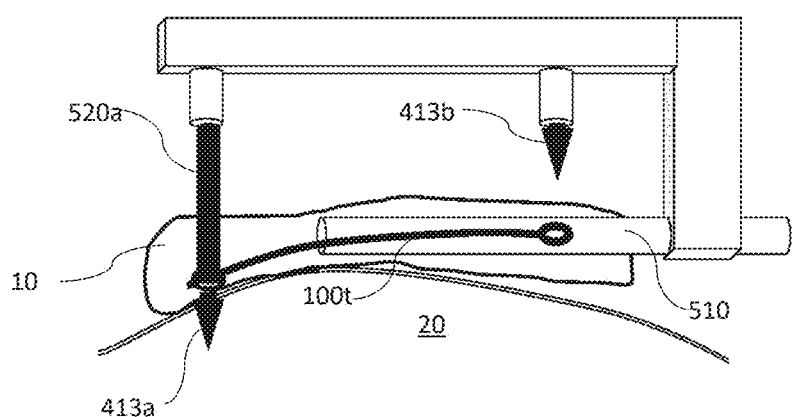
Figure 14C:
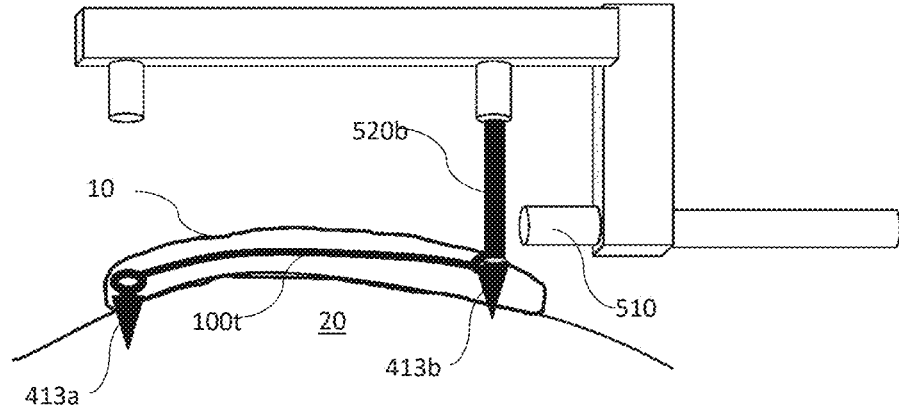

In some embodiments, a guide 500 may be used to insert the soft tissue engagement device 100 and/or one or more anchors. FIGS. 14A to 14C illustrate an exemplary embodiment of a guide which assists in achieving alignment and proper placement of a soft tissue engagement device 100*t* with anchors 413*a* and 413*b*. In FIG. 14A, the device 100*t* is inserted through the tendon 10, transverse to the load bearing direction using arm 510. As shown in FIG. 14B, anchor 413*a* is subsequently placed using punch 520*a*, through the tendon 10 and through anchor receiving aperture 135*a* of the device 100*t* and into the bone 20. Anchor 413*b* is similarly placed, as shown in FIG. 14C, using punch 520*b*. It will be appreciated that, in this embodiment, the need for sutures is eliminated as the device 100*t* engages the anchors 413*ab* directly.

In some embodiments, one or more tissue engagement devices may be used to attach one severed end of a soft tissue structure to another severed end. For example, the device may be used to reattach ends of a severed tendon or ligament. In such embodiments, a first tissue engagement device may be inserted into the tissue of a first severed end of the tissue, while a second tissue engagement device may be inserted into a second severed end of the tissue. Sutures may then be passed through the tissue, around the tissue engagement devices and tied to form one or more loops, securing the severed ends of the tissue to each other. As with the soft-tissue to bone connection, the tissue engagement device may improve resistance to suture cut-out or "cheese wiring" of the sutures through the tissue and thereby improve the tensile strength of the repair.

Figure 12:
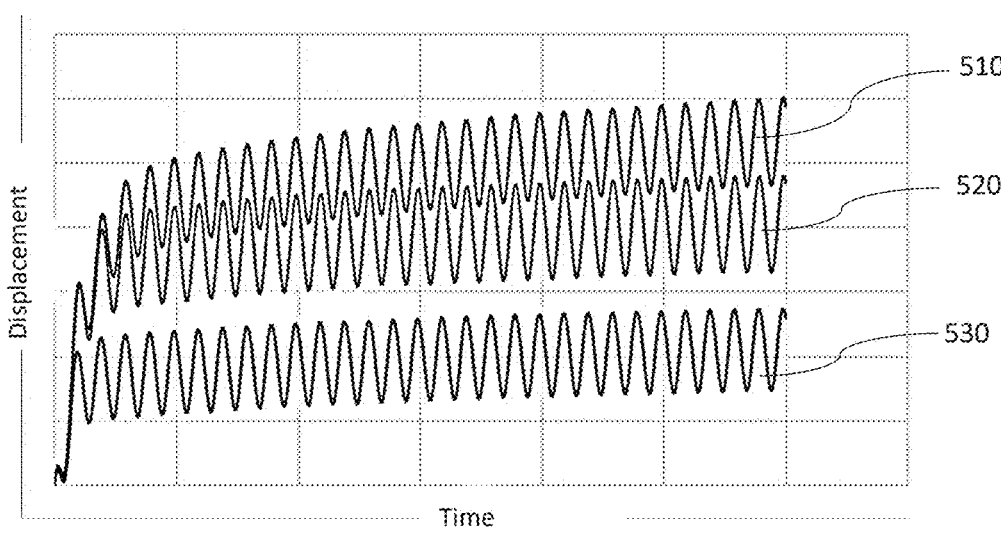
FIG. 12 shows load-displacement curves obtained during cyclic load testing of tendon connections to bone according to two embodiments of the present disclosure, compared to a suture-only repair.

FIG. 12 shows load-displacement curves for three tendon repairs subjected to cyclic loading of 5 to 50 N. Curve 510 corresponds to a control tendon repair, constructed using medial and lateral rows of bone anchors connected by a suture bridge. Curve 520 corresponds to a tendon repair constructed using a tissue engagement device according to the present disclosure, in combination with medial and lateral rows of bone anchors connected by a suture bridge (for example, as shown in FIGS. 8 and 9). Curve 530 corresponds to a to a tendon repair constructed using a tissue engagement device according to the present disclosure, in combination with a medial row of bone anchors only (for example, as shown in FIG. 11). Comparing, curves 520 and 530 to the control 510 shows that repairs constructed with the tissue engagement device of the present disclosure are more rigid than the control, and exhibit less creep over repeated cycles. The increase in creep in the control 510 is due to damage to the tendon as the sutures "cheese wire" through the tissue. Further, it is evident that the repair using medial anchors only (curve 530) is more rigid than the repair using both medial and lateral anchors, due to the reduced suture length.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A method of attaching a soft tissue to a bone, the method comprising:

inserting a soft tissue engagement device into the soft tissue transverse to a load bearing direction of the soft tissue, wherein the soft tissue engagement device comprises a substantially rigid elongate body extending from a first end to a second end, the elongate body configured to engage sutures attached to one or more suture-anchors secured to a bone, the one or more suture anchors including one or more first suture anchors;

passing the sutures from the one or more suture anchors through the soft tissue medially relative to the soft tissue engagement device;

passing the sutures over the soft tissue engagement device; and subsequently, securing each of the sutures to one of the one or more first suture anchors or to one of one or more second suture anchors.

2. The method of claim 1, wherein the soft tissue is a tendon or a ligament.

3. The method of claim 1, wherein the one or more first suture anchors comprise one or more medial anchors and the one or more second suture anchors comprise one or more lateral anchors.

4. The method of claim 3, wherein the one or more medial anchors are positioned inferiorly to the soft tissue engagement device in an underlying bone.

5. The method of claim 3, wherein the method further comprises:

fastening a first medial anchor of the one or more medial anchors to the bone;

fastening a second medial anchor of the one or more medial anchors to the bone, the second medial anchor spaced from the first medial anchor;

fastening a first lateral anchor of the one or more lateral anchors to the bone at a location lateral to the first and second medial anchors;

fastening a second lateral anchor of the one or more lateral anchors to the bone, the second lateral anchor spaced from the first lateral anchor, wherein the sutures include a first suture and a second suture, the first suture having a fixed end and a free end, wherein the fixed end of the first suture is secured to the first medial anchor, the second suture having a fixed end and a free end, wherein the fixed end of the second suture is secured to the second medial anchor;

passing the free end of the first suture through the soft tissue medial to the tissue engagement device, over the tissue engagement device and through the tissue in a direction lateral to the tissue engagement device and securing the free end of the first suture to the first lateral anchor; and passing the free end of the second suture through the soft tissue medial to the tissue engagement device, over the tissue engagement device and through the tissue in a direction lateral to the tissue engagement device and securing the free end of the second suture to the second lateral anchor.

6. The method of claim 5, wherein the sutures include a third suture having a fixed end and a free end, the fixed end of the third suture secured to the first medial anchor and a fourth suture having a fixed end and a free end, wherein the fixed end of the fourth suture is secured to the second medial anchor, the method further comprising:

passing the free end of the third suture through the soft tissue medial to the tissue engagement device, over the tissue engagement device and through the tissue in a direction lateral to the tissue engagement device and securing the free end of the third suture to the second lateral anchor; and passing the free end of the forth suture through the soft tissue medial to the tissue engagement device, over the tissue engagement device and through the tissue in a direction lateral to the tissue engagement device and securing the free end of the forth suture to the first lateral anchor.

* * * * *